United States Patent [19]

Gutierrez et al.

[11] 4,424,171

[45] Jan. 3, 1984

[54] AQUEOUS STORAGE SYSTEMS FOR STORAGE OF GROUND GUAYULE PLANT MATERIAL

[75] Inventors: Richard Gutierrez, Canal Fulton; Edward L. Kay, Akron, both of Ohio

[73] Assignee: The Firestone Tire & Rubber Company, Akron, Ohio

[21] Appl. No.: 355,078

[22] Filed: Mar. 5, 1982

[51] Int. Cl.$^3$ ............................................. C08L 7/02
[52] U.S. Cl. ................................. 524/414; 524/401; 524/422; 524/423; 524/417; 524/424; 524/426; 524/530; 524/433; 524/436
[58] Field of Search ............... 260/814, 815, 819, 820; 528/487, 489

[56] References Cited

U.S. PATENT DOCUMENTS

| | | | |
|---|---|---|---|
| 1,753,184 | 4/1930 | Spence | 260/816 |
| 1,757,632 | 5/1930 | Hazell | 260/820 |
| 2,665,317 | 1/1954 | Clark et al. | 260/818 |

*Primary Examiner*—Paul R. Michl
*Attorney, Agent, or Firm*—Daniel N. Hall

[57] ABSTRACT

Guayule plant material can be stored in an aqueous system comprising (a) communited guayule plant material; (b) water and (c) an odor inhibitor. Typical inhibitors include protanic acids, acid salts, metal oxides and metal hydroxides. These storage systems permit efficient operation of guayule processing facilities while minimizing odors often developed in stored plant material.

11 Claims, No Drawings

AQUEOUS STORAGE SYSTEMS FOR STORAGE OF GROUND GUAYULE PLANT MATERIAL

FIELD OF THE INVENTION

This invention relates to systems for storage of guayule plant material. More particularly it relates to aqueous systems for storage of ground guayule material before, during and after processing. These systems are chemically inhibited against development of noxious odors usually associated with stored, uninhibited plant material.

BACKGROUND OF THE INVENTION AND PRIOR ART

There is a need for a practical and effective process and system for the storage of ground (communited) guayule shrub. Commercial processing plants to recover valuable guayule rubber, resin and other products are operated most efficiently on a continuous basis. It is well known that intermittent operation of such plants is costly in terms of operating expenses as well as lost production of products. Productivity decreases and energy costs increase if a guayule processing plant has to be shut down or interrupted because of raw material shortages. Disruptions of continuous, adequate supply of guayule shrub raw material may well result from weather conditions which interfer with shrub harvesting. Such interruptions may be short term or relatively prolonged. In any event, it is clear that an adequate, continuous supply of plant material is desirable for a guayule processing plant.

To provide such continuous supplies, it is necessary to have a system to store the guayule material before, during and after processing. It is well known in industry that space alloted for raw material storage can significantly add to production costs. For all these reasons, attention has been directed to the discovery of a system and process that would be effective for storage of ground guayule shrub. Although storage of whole (unground) guayule material might be preferred because of the relatively low surface area of the shrub exposed to the atmosphere, economics are greatly improved if the shrub is first ground. Ground material requires less storage space than the bulky whole shrub. In addition, unground, pollarded guayule shrub is much more difficult to transfer during processing. The bulk handling of essentialy free flowing ground material shrub is greatly preferred over the handling of low density, bulky, whole or pollarded guayule shrub.

Temporary storage of untreated, unprotected ground plant material is feasible; from a practical standpoint, however, storage time is severely limited because of changes in and deterioration of the constituents of the guayule shrub. Storage time can be increased somewhat by storing the ground material under inert gas, but again this is expensive and, from a technical standpoint, the displacement of all the air and, especially, oxygen, from the stored shrub is a difficult, if not impossible process. This problem is aggravated because considerable oxygen can be adsorbed in the porous plant requiring excessive amounts of inert gas to flush it out.

In addition to the above problems associated with storage under inert gas, a very practical problem is compaction of the ground shrub under its weight. Furthermore, during the grinding of the guayule shrub, resins are released which tend to bind the ground shrub particles together. If even a small amount of moisture is present in the shrub, simple sugars present in the shrub can also increase binding of shrub particles.

Many of the aforementioned difficulties associated with storage of ground guayule shrub were recognized and reported by researchers at the Salinas Natural Rubber Research Station (U.S. Natural Rubber Research Station; Final Report: Natural Rubber Extraction and Processing Investigations; Bureau of Agriculture and Industrial Chemistry, U.S.D.A., April, 1953).

SUMMARY OF THE INVENTION

A practical and efficient process and system for storage of ground guayule shrub has now been discovered. Development of offensive odors, as well as microfloral growth usually associated with such odors during prolonged storage of ground guayule shrub, is essentially eliminated by practice of the invention.

According to the invention, there is provided an aqueous guayule plant material storage system comprising: (a) comminuted guayule plant material; (b) water; and (c) at least one inhibitor of offensive odor development selected from the group consisting of protonic acids, acid salts, metal oxides and metal hydroxides. The plant material stored can be defoliated or non-defoliated. An additional advantage of the inventive guayule storage systems is that the ground shrub/aqueous slurries produced can be pumped in closed conduits from one process unit to another, thus avoiding undue exposure of the ground shrub to air. A more uniform discharge of shrub from storage is realized because water functions as a vehicle to aid its discharge. Some agitation of the shrub slurry is desirable and aids further processing.

DETAILED DESCRIPTION OF THE INVENTION

Generally, guayule shrub received at a processing plant from a cultivation area will be whole, pollarded (that is, the top portion of the shrub only) or crudely chopped to reduce bulk density. The shrub may or may not be defoliated and, in addition, it may or may not be air-dried. Regardless of the exact physical state in which the shrub is received at the processing plant, the inventive process requires that the shrub be ground, typically, for example, with a hammermill, to an appropriate small particle size typically in the range of about 0.06–0.25 inch nominal particle size. It is then charged to a suitable vessel for storage. The vessel may contain water adjusted to a pH in the ranges disclosed below or, optionally, the ground shrub and water (adjusted to the disclosed pH ranges) may be simultaneously charged to the storage vessel to aid in the mixing process. An optional procedure is to form a shrub/water slurry and then adjust the pH. Usually the storage vessel is provided with suitable agitation so that a uniform slurry of ground guayule shrub in the inhibited water is produced.

It is usually not necessary to agitate the inhibited guayule shrub/water slurry during storage; it is sometimes useful, however, to agitate the shrub slurry just prior to processing the shrub for recovery of resinous guayule rubber. This insures that a uniform slurry is pumped to the appropriate processing unit (such as a pulping mill) without undue exposure to air.

An alternative procedure is to deresinate the ground shrub with an appropriate resin solvent such as anhydrous acetone. Such processes are known; see, for example, U.S. patent application, Ser. No. 298,447 which is incorporated by reference herein for its disclosures relating to deresination of guayule with solvents such as acetone. The deresinated shrub is then freed of solvent before being stored in the inhibited aqueous storage system described above. In effect then, there are at least two means of practicing the invention: (1) freshly harvested material can be stored until fully processed to recover rubber and, optionally, resin; or (2) shrub can be first deresinated and then the deresinated material stored until further processed to recover rubber.

Odor development in the inventive storage systems is inhibited by inclusion of at least one inhibitor which provides the desired pH. The pH of the system is adjusted by adding an appropriate amount of acidic or basic inhibitor. Generally these materials are acids or bases through acidic or basic salts can be used, particularly when buffer effects are desired. Typical acids include mineral acids such as sulfuric and phosphoric acids and Group IA and IIA alkali and alkaline earth oxides and hydroxides. Salts such as Group IA and IIB acid sulfates, acid sulfites, acid phosphates and acid carbonates can also be used. Mixtures of appropriate materials can also be employed. The inhibitors can be used in amounts sufficient saturate the aqueous system at the storage temperature, if desired, but this is not necessary. For reasons of economy, convenience and availability, sulfuric acid and lime (CaO) are often used as inhibitors.

The above-noted beneficial effects of the invention are shown by the following specific examples which illustrate but do not in any way restrict the scope of the invention.

EXAMPLE I; STORAGE OF GROUND GUAYULE SHRUB UNDER VARIOUS GASES

To provide a basis for comparison of various storage conditions, freshly ground guayule shrub is stored in air and under inert gases such as nitrogen and carbon dioxide. The nitrogen sample is prepared by purging ground guayule material with nitrogen to displace air. The carbon dioxide sample is prepared by placing the ground shrub over solid carbon dioxide (dry ice) and allowing vapor to displace the air present. Continuous purge with either nitrogen or carbon dioxide is not provided. Doubtlessly such a purge would be more effective but also more costly.

The samples stored under the above-described conditions are periodically observed and the development of offensive odors and microfloral growth recorded. Because odor is subjective and difficult to quantify, an arbitrary numerical rating is used to describe odor development (see Table I). Microfloral growth ratings are based on visual inspection. Although microfloral growth per se may not deleterious to effective storage, the microfloral growth observed in the storage examples is usually associated with an offensive odor.

Referring to Table I, it is seen that ground guayule shrub stored without protection from the atmosphere develops an objectionable odor after one week. After one month, the odor is nauseating. A trace of microfloral growth is observed after one week; the microfloral growth is much heavier after one month. Storage of the ground guayule shrub under nitrogen or carbon dioxide results in the same "one week" observations; after one month, however, both samples are "very objectionable" in odor and found to have moderate microfloral growth.

As previously stated, a continuous purge of nitrogen or carbon dioxide is not provided nor is a positive pressure of the inert gases maintained. Either or both procedures should improve the storage stability of the ground guayule shrub; such improvements, however, are too costly for practical commerical use. In addition, as noted above, the U.S.D.A. April, 1953, Final Report described the difficulty of uniformly discharging ground guayule shrub from silo storage.

EXAMPLE II; STORAGE OF GROUND GUAYULE SHRUB UNDER WATER CONTAINING SELECTED ADDITIVES

It is found that a liquid vehicle aids in the uniform discharge of ground guayule shrub from a storage vessel. Another advantage of this procedure that the liquid/shrub slurry can be easily transferred to various processing units thus avoiding unnessary exposure of the plant material to the atmosphere. Discharge of the liquid/shrub slurry is facilitated if it is first agitated.

The preferred liquid for storage is water. It is found, however, that water alone is no more effective than nitrogen or carbon dioxide in preventing offensive odor development and microbiological growth during long-term storage.

The addition of selected chemical inhibitors to the water prevents development of offensive odor and microfloral growth.

Aqueous solutions (or suspensions) of selected inhibitors and ground guayule shrub are prepared in the liquid. Specifically, 0.02 grams of selected solid additive is added to 200 cc of distilled water and 20 grams of nominal $\frac{1}{8}$ inch ground guayule shrub is combined with the mixture. With liquid additives, 0.02 cc of the additive is added to the water. The samples are contained in glass containers, loosely fitted with covers to retard evaporation. The first microfloral growth appears as a white material on the surface of the sample. After prolonged storage (especially if the sample is agitated), however, the white growth progressively darkens to a dark-brown, almost black slime or sludge. In addition, the appearance of microbiological growth generally is associated with the development of an offensive odor; Some samples, however, containing growth do not develop such odors. Since the invention concerns primarily the prevention of offensive odors in guayule shrub storage systems, the appearance of growth is considered of secondary importance. It is primarily the odors which discourage processing plant personnel and, more generally, foul the environment and make guayule storage objectionable.

Periodic sample observations are made using the same ratings for odor and microbiological growth development described in Table I. These observations are summarized in Table II. The additives selected are grouped according to their general chemical characteristics.

Referring to the data in Table II, it is seen that storage of guayule shrub under water (Sample 1) showed no advantage over storage under nitrogen or carbon dioxide (see the ratings in Table I).

Samples 2 and 3, containing ammonia and sodium bisulfite, respectively, show no improvement over water alone after two months storage. Ammonia is selected because it can be used to stabilize Hevea rubber latex. Sodium bisulfite is soluble in water and can be relatively easily oxidized to sulfate thereby scavenging oxygen from the system.

Samples 4, 5 and 6, which contained, respectively, isopropanol, DBPC (di(tertiarybutyl)-p-cresol) and PPD (an N-alkyl-N'-aryl-p-phenylenediamine), are no more effectively inhibited than the control. Isopropanol is chosen because of its ability to kill microorganisms. DBPC and PPD are known rubber anti-oxidants.

Sample 7, containing oxalic acid, has an offensive odor after one week and one month storage; after two months storage, however, the odor is similar to the odor observed in the other samples having a low pH. Microbiological growth is also observed in the oxalic acid sample.

Sample 8, containing acetic acid, originally has a vinegary odor; after approximately one week storage, however, the odor changes to a mild, somewhat "sweet" one which is unobjectionable. Microbiological, probably microfloral, growth appears in Sample 8 after about two months.

Samples 9, 10 and 11, containing strong mineral acids such as hydrochloric, sulfuric and phosphoric acids, respectively, are effectively inhibited with both objectionable odors and microfloral growth after one month storage. After two months, microfloral growth appears in samples 9 and 11. It should be emphasized that the odor in these samples is mildly sweet and unobjectionable. Sulfuric acid is relatively inexpensive, readily available and non-volatile. Phosphoric acid has the same advantages as sulfuric acid; in addition, its disposal could provide, after neutralization, a desirable fertilizer.

Samples 12 and 13 contain salts of a weak base, ($NH_4OH$), and strong acids, sulfuric and phosphoric, respectively. As noted in Table II, these inhibitors are somewhat less effective than the respective free acids but still useful.

Samples 14, 15, 16 and 17, containing, respectively, sodium hydroxide, acid carbonate, carbonate and sulfate, show the effects of selected anions (keeping the sodium cation constant) on development of offensive odor and microbiological growth. As shown in Table II, Sample 14, containing sodium hydroxide, is well stabilized in contrast to Samples 15, 16 and 17.

On the basis of the data summarized above, it can be concluded that the development of offensive odors during storage of ground guayule shrub in aqueous systems can be controlled by controlling the system's pH.

Strong mineral acids resulting in low pH's are effective and strong bases (such as sodium hydroxide), which produce high pH values, are also effective. Therefore, the pH of the aqueous systems listed in Table II are shown in an attempt to correlate inhibition effectiveness with pH. Samples containing calcium oxide, calcium carbonate and magnesium oxide are also included in Table II, as samples 18, 19 and 20, respectively. These additives contain divalent cations which may effect microfloral growth differently than the previously evaluated monovalent salts. These oxides, of course, readily react with water to form the analogous hydroxides.

As noted in Table II, calcium and magnesium oxides (actually the hydroxides) effectively prevent formation of offensive odors and microbiological growth; calcium carbonate acts to a similar but lesser extent.

It should be noted that the solubility of calcium hydroxide in water at 0° C. is 0.185 parts per 100 part of water and decreases to 0.088 parts per 100 parts water at 100° C. The solubility of magnesium hydroxide in water at 18° C. is only 0.0009 parts magnesium hydroxide in 100 parts water. Based on these facts, sample 20 contains more magnesium oxide (hydroxides) than needed to saturate it and very little of the calcium oxide (hydroxide) is required for effective stabilization. In evaluating calcium and/or magnesium oxides, one notes calcium oxide is very inexpensive, while magnesium oxide is known to effect some stabilization of rubber. Both compounds are effective in stabilizing aqueous slurries of ground guayule against offensive odor development.

EXAMPLE III; CORRELATION OF ADDITIVE EFFECTIVENESS WITH MEDIUM pH

An attempt is made to correlate inhibition effectiveness with system pH. The pH values for the various systems investigated are shown in Table II. These values are determined using a Fisher Accunet ® pH meter, Model 600 using a calomel glass reference electrode. The meter is calibrated at pH 4 and 7 before and after testing.

Referring to the pH values shown in Table II, it should be noted that some of them are determined after one day storage and the remaining ones, after 34 days storage. As noted in the control sample containing only water (No. 1), a slight increase in pH was noted during storage, namely, 6.1 to 7.2. Therefore, the pH data in Table II are reasonably accurate and establish the pH limitations necessary to ensure adequate stabilization of aqueous guayule storage systems.

Again referring to the pH data in Table II, it is noted that the strong mineral acids, hydrochloric, sulfuric and phosphoric (Samples 9, 19 and 11, respectively) had pH values of 1.7, 1.4 and 2.3, respectively. These samples are stabilized against development of offensive odors. The only odor that develops is a mild, somewhat sweet odor which is unobjectionable. Some microfloral growth is present in the hydrochloric and phosphoric acid samples after two months.

The organic acid samples (oxalic and acetic; Samples 7 and 8, respectively) had pH values of 3.7 and 4.2. The oxalic sample (No. 7) initially develops a somewhat offensive odor; however, after two months storage, the door is mild and somewhat sweet. Initially, the acetic sample has the odor of vinegar but with time this changes to a mild, somewhat sweet odor. Microfloral growth is more pronounced in the oxalic acid sample. Sample 8 (acetic acid) develops some microfloral growth after two months storage.

The pH of effective aqueous storage systems is less than about 5.0 usually less than about 4.5, and preferably, less than 2.5 to prevent development of offensive odors and deterioration.

As shown in Table II, Samples 14, 18 and 20, containing, respectively, sodium hydroxide, calcium oxide and magnesium oxide, have pH values of 9.1, 11.9 and 10.2. No offensive odors and essentially no microfloral growth are observed in these samples after prolonged storage. Therefore, systems having pH values of greater than about 9 clearly exhibit stability. Broadly, a pH of greater than about 8.5 is adequate. It is also seen that microfloral growth tends to turn brown-black after greater than one month storage with the growth appearing as a semi-solid cake or slime. In the samples containing mineral acids (Sample 9, 10 and 11), as well as the sample containing acetic acid (No. 8), a mild, somewhat sweet odor develops which is unobjectionable.

In summary, it is found that offensive odor development in aqueous storage systems containing ground guayule shrub can be effectively controlled if the pH of the system is less than about 4.5 or greater than about 8.5. Many ways of maintaining the pH of the aqueous system in this range are known; considering, however, the cost of treatment, availability of the additives and possible effects on the environment upon discharge of the aqueous medium, the alkaline earth oxides such as calcium oxide and magnesium oxide are preferred for pH's over about 8.5.

For similar reasons, sulfuric and/or phosphoric acid are preferred for pH's less than about 4.5.

TABLE I

Observations on Development of Offensive Odor and Microfloral Growth on Samples of Ground Guayule Shrub Stored under Various Gas Atmospheres

| Ground Shrub | Ambient Temperature (25° C.) Storage, After | | | | | |
|---|---|---|---|---|---|---|
| | 1 Day | | 1 Week | | 1 Month | |
| Stored in | Odor | MFG # | Odor | MFG # | Odor | MFG # |
| Air | 0 | 0 | 1 | 1 | 3 | 3 |
| Nitrogen | 0 | 0 | 1 | 1 | 2 | 2 |
| Carbon Dioxide | 0 | 0 | 1 | 1 | 2 | 2 |

MFG = Microfloral Growth
Significance of Numerical Ratings:

| Odor | Microfloral Growth |
|---|---|
| 0 - Original odor | 0 - None |
| 1 - Somewhat objectionable | 1 - Trace growth on surface |
| 2 - Very objectionable | 2 - Moderate growth on surface |
| 3 - Nauseating | 3 - Heavy growth appears under surface |

TABLE II

Observations on Development of Offensive Odor and Microfloral Growth on Samples of Ground Guayule Shrub Stored under Water Containing Selected Additives Correlation with pH of Aqueous Systems

| Ground Shrub | Ambient Temperature (25° C.) Storage, After | | | | | | | | |
|---|---|---|---|---|---|---|---|---|---|
| | ca. 1 Week | | ca. 1 Month | | ca. 2 Months | | ca. 3 Months | | |
| Stored in | Odor | MFG | Odor | MFG | Odor | MFG | Odor | MFG | pH |
| 1. Water | 1 | 1 | 3 | 3 | 3 | 3 | 3 | 3[b] | 6.1–7.2 |
| Water Plus: | | | | | | | | | |
| 2. Ammonia | 1 | 1 | 2 | 3 | 3 | 3 | — | — | — |
| 3. NaHSO$_3$ | 1 | 1 | 2 | 3 | 3 | 3 | — | — | — |
| 4. Isopropanol | 1 | 1 | 3 | 3 | 3 | 3 | 3 | 3[b] | 7.0 |
| 5. DBPC | 1 | 2 | 3 | 3 | 3 | 3 | 3 | 3[b] | 7.6 |
| 6. PPD | 1 | 1 | 3 | 3 | 3 | 3[b] | — | — | 6.1[a] |
| 7. Oxalic | 2 | 2 | 2 | 3 | 1# | 3[b] | 1— | 3[b] | 3.7 |
| 8. Acetic | 1# | 0 | 1# | 0 | 1# | 1[c] | — | — | 4.2[a] |
| 9. Hydrochloric | 1# | 0 | 1# | 0 | 1# | 1[c] | — | — | 1.7[a] |
| 10. Sulfuric | 0# | 0 | 0# | 0 | 1# | 0 | 1# | 0 | 1.4 |
| 11. Phosphoric | 1# | 0 | 1# | 0 | 1# | 1[d] | — | — | 2.3[a] |
| 12. (NH$_4$)$_2$SO$_4$ | 1 | 2 | 1 | 3 | 3 | 3[b] | — | — | 6.5[a] |
| 13. NH$_4$H$_2$PO$_4$ | 1 | 2 | 1 | 2 | 2 | 3[b] | — | — | 5.8[a] |
| 14. NaOH | 0 | 0 | 0 | 0 | 0 | 1 | 0 | 1[d] | 9.1 |
| 15. NaHCO$_3$ | 1 | 1 | 3 | 3 | 2 | 3 | 1 | 3[b] | 8.9 |
| 16. Na$_2$CO$_3$ | 0 | 0 | 3 | 3 | 1 | 3 | 1 | 3[b] | 9.3 |
| 17. Na$_2$SO$_4$ | 2 | 2 | 3 | 3 | 3 | 3 | 3 | 3[b] | 6.9 |
| 18. CaO | 0 | 0 | 0 | 0 | 0 | 0 | 0 | 0 | 11.9 |
| 19. CaCO$_3$ | 1 | 1 | 3 | 3 | 2 | 2 | 2 | 3[b] | 6.7 |
| 20. MgO | 0 | 0 | 0 | 0 | 0 | 0 | — | — | 10.2 |

[1]Original odor and no "MFG" (microfloral growth) observed on all samples after one day.
[a]pH determined after one day storage; all other pH values determined after 34 days storage.
Mild, somewhat "sweet" odor; not objectionable
[b]Initial microfloral growth is white but, after additional storage time, the growth darkens and eventually becomes a black slime.
[c]Initial microfloral growth is white but, after additional storage time, the growth decays leaving a light tan liquid over the ground shrub.
[d]Initial microfloral growth is white but, after additional storage time, the growth decays leaving a black-gray growth on the liquid surface. The supernatant liquid is tan.

What is claimed is:

1. An aqueous guayule plant material storage system comprising:
   (a) comminuted guayule plant material;
   (b) water; and
   (c) at least one inhibitor of offensive odor development selected from the group consisting of protonic acids, acid salts, metal oxides and metal hydroxides.

2. The system of claim 1 wherein the system has a pH of less than about 5.0 or greater than about 8.5.

3. The system of claim 2 wherein the system has a pH of less than about 4.5 and the inhibitor is phosphoric acid, sulfuric acid and mixtures thereof.

4. The system of claim 2 wherein the system has a pH greater than about 9 and the inhibitor is a Group IA or IIA metal oxide, hydroxide or mixture thereof.

5. The system of claim 4 wherein the inhibitor is a CaO, Ca(OH)$_2$, MgO, Mg(OH)$_2$ or a mixture thereof.

6. The system of claim 2 wherein the inhibitor is a metal salt selected from the group consisting of group IA and IIA acid phosphate, acid carbonates, acid sulfates, and mixtures thereof.

7. The system of claim 5 wherein the inhibitor is present in an amount sufficient to saturate the system at the storage temperature.

8. A method of storing comminuted quayule plant material which, in any order of stems, comprises:
   (a) forming an aqueous slurry of the material with water;

(b) adding to the water at least one inhibitor of odor selected from the group consisting of protonic acids, metal acid salts, metal oxides, and metal hydroxides, which makes the pH of the system greater than about 8.5 or less than about 5.0.

9. The method of claim 8 wherein the inhibitor is selected from the group consisting of, metal oxides and metal hydroxides.

10. The method of claim 9 wherein the inhibitor is CaO, Ca(OH)$_2$, MgO, Mg(OH)$_2$ or a mixture thereof.

11. The method of claim 10 wherein the inhibitor is present in an amount sufficient to saturate the system at the storage temperature.

* * * * *